United States Patent [19]

Blum et al.

[11] Patent Number: 4,761,429
[45] Date of Patent: Aug. 2, 1988

[54] ENKEPHALINASE AND ENDORPHINASE INHIBITORS AS ANTI-CRAVING COMPOSITIONS

[76] Inventors: Kenneth Blum, 3707 Castle Crest, San Antonio, Tex. 78230; Arthur H. Briggs, 707 Serenade, San Antonio, Tex. 78216; Jack E. Wallace, 9215 George Kyle, San Antonio, Tex. 78240

[21] Appl. No.: 757,733

[22] Filed: Jul. 22, 1985

[51] Int. Cl.$^4$ ............................................. A61K 31/195
[52] U.S. Cl. ..................................................... 514/561
[58] Field of Search ......................................... 514/561

[56] References Cited

U.S. PATENT DOCUMENTS 4,439,452  3/1984  Ehrenpreis ......................... 514/561

OTHER PUBLICATIONS

Goldstein and Judson, Science, 172:290-292 (Apr. 1971).
Miceli, Eur. J. Pharmacol., 63:327-33 (1980).
Jorgensen and Hole, Eur. J. Pharmacol., 75:223-229 (1981).
Jorgensen and Hole, Eur. J. Pharmacol., 125:249-56 (1986).
Catley, Lancet 1263 (Jun. 6, 1981).
Altschuler, et al., Pharmacol., Biochem. & Behav., 14:97-100.
Galizio, et al., Alcohol, 1:197-200 (1984).
Nuotto, et al., Acta Pharmacol. Toxicol. 54:278-84 (1984).
Lignian, et al., Human Toxicol., 2:221-25 (1983).
Ewing and McCarty, Alcoholism, 7:271-5 (1983).
Hemningsen and Sorenson, Acta Pharmacol. et. Toxicol, 46:62-65 (1980).
Winter, Psychopharmacol. (Berl.), 44:209-14 (1975).
Saddler, et al., Clin. Exper. Pharmacol, & Physiol., 12:359-64 (1985).
Blum, et al., Nature, 265:49 (1977).
Blum, et al., Subst. Alcohol Act./Misuse, 1:327-334 (1980).
Kiianmaa, et al., Phychopharmacol., 79:291-294 (1983).
Blum, et al., Chapter 15 in Alcohol Tolerance and Dependence (1980).
Blum, et al., Pharmacologiest, 17:197 (1975).
Altschyler, et al., Life Sci., 26:679-688 (1980).
Pillai and Ross, Alcohol, 3:249-53 (1986).
McGivern, et al., Substance an Alcohol Actions/Misuse 1:335-42 (1980).
Jeffcoate, et al., Pharmacol. Biochem. & Behav., 13: (Suppl. 1):145-148 (1980).
Ewing, et al., Adv. Sub. Abuse, 3:47-59 (1984).
Shippenberg an Altshuler, Alcohol, 197-201 (1985).
Mackenzie, Lancet, 733 (Mar. 31, 1979).
Jeffcoate, et al., Lancet, 1157 (Dec. 1, 1979).
Jeffereys, et al., Lancet, 308 (Feb. 9, 1980).
Blum, et al., Subst. Alc. Act./Mis. 3:1-4 (1982).
Siegel, Subst. Alc. Act/Misuse, 3:303-5 (1983).
Reid and Hunter, Alcohol, 1:33-37 (1984).
Nicholas an Tsiao, Science, 157:561-3 (1967).
Hubbell, et al., Alcohol, 4:149-156 (1987).
Beaman, et al., Alcohol, 1:39-42 (1984).
Ho, et al., in Alcohol and Opiates 189-202 (Blum, ed., 1977).
Ross, et al., Proc. West. Pharmacol. Soc., 19:326-330 (1976).
Gelfand and Ammit, Nature, 259:415 (1976).
Blum, et al., Experentia, 32:79 (1976).
Seevers, Science, 113 (Dec. 4, 1970).
Davis and Walsch, Science, 167:1005 (1970).
Ross, et al., Science, 186:63-65 (1974).
Blum, et al., Science, 216:1425-26 (1982).
Genazzani, et al., J. Clin. Endocrinol, Metah., 55:583 (1982).
Blum, et al., Experentia, 38:1469-70 (1982).
Blum, et al., PNAS, 80:6510-12 (1983).
Govoni, et al., Alcohol and Drug Res. 7:93-98 (1986).
Ho an Rossi, J. Pharm. Pharmacol. 34:118-19 (1981).
Blum in Central and Peripheral Endorphins 339 (1984).
Ryder, Peptides, 2:223-26 (1981).
Schulz, Psychopharmacology, 668:221-27 (1981).
Pfeiffer, et al., Neuropharmacol., 20:1229-32 (1981).
Hiller, et al., Science, 214:468-69 (1981).
Lord, et al., Nature, 267:495-498 (1977).
Kerchner and Geary, J. Pharmacol. Exper. Therap., 236:33 (1983).
Van Amsterdam, et al., Life Sciences, Suppl. I, 33:109 (1983).
Hunter, et al., Alcohol, 1:43-46 (1984).
Barbaccia, et al., Psychopharmacol., 74:260-62 (1981).
Carlsson and Lindquist, J. Pharm. Pharmac. 25:437-440 (1973).
Patterson, et al., J. Bioelec., 3(1&2):193-221 (1984).
Charness, M. E., et al., Science 222, 1246-1248.
Blum, et al., Alcohol and Drug Research, 6:455-61 (1985).

Primary Examiner—Stanley J. Friedman
Attorney, Agent, or Firm—Iver P. Cooper

[57] ABSTRACT

A new class of anti-craving compositions is provided by substances which inhibit breakdown of endogenous substances such as enkephalins and/or endorphins. An anti-alcohol craving effect is observed with an enkephalin breakdown inhibitor. Specifically, D-phenylalanine, DL-phenylalanine, D-leucine, DL-leucine, and hydrocinnamic acid, each an encephalin breakdown inhibitor, significantly lowered alcohol intake in animals and humans. The anti-alcohol desire effect is observed in animals genetically prone to choose alcohol over water solutions.

8 Claims, No Drawings

ENKEPHALINASE AND ENDORPHINASE INHIBITORS AS ANTI-CRAVING COMPOSITIONS

BACKGROUND OF THE INVENTION

1. Field of the Invention

This invention, in part, relates to anti-craving as mediated by substances which reduce the desire for euphoriants, specifically alcohol and opiates. In this invention craving means obsessive compulsion, excessive desire for and indulgence in substances which are classed as psychoactive drugs and/or act which enhance the effect of endogenous and/or exogenous neuropeptides, neurotransmitters and psychoactive agents, respectively. Psychoactive drugs include but are not limited to alcohol, opiates, and food. Anti-craving medicaments result in a reduction in the excessive behavior desired. Substances which prevent the destruction or enhance the content or action of brain chemicals, enkephalins, endorphins, opioid transmitters, opioid receptors are described as anti-craving agents. Furthermore, in this application the term neuropeptidyl opiates (NPO) includes both brain endorphins and enkephalins; and an euphoriant includes but is not limited to alcohol, opiates, nicotine, food and sexual acts.

More particularly, this invention relates to a treatment of animals and humans by administering substances which inhibit and/or delay the inherent breakdown of a class of naturally occurring peptidyl opiates or euphoriants that are created and exist within mammals as well as altering the function and content of other neurotransmitter substances which interact with the endorphinergic transmitter systems in the nervous system and with opioid receptor function. Such neurotransmitter substances include but are not limited to glutamine, gamma-amino-butryic-acid (GABA), serotonin, and norepinephrine.

2. Description of the Prior Art

Enkephalins and endorphins are opiate-like substances which have recently been discovered to be endogenous in various animal species, including mammals and man, whereby the general term endorphins includes but is not limited to B-endorphin, methionine-enkephalin, and leucine-enkephalin. Enkephalins and endorphins are peptides and/or polypeptides normally present in the brain.

As pointed out in U.S. Pat. No. 4,439,452, it has heretofore been observed that enkephalins and endorphins have an ability to act as analgesics when administered to various animals and humans by certain special routes, including intracerebral injections. The major drawbacks of utilizing these endogenous substances directly for therapeutic purposes are their extremely labile nature and poor penetration into the brain via oral administration. It is known that the destruction of the endogenous enkephalins and/or endorphins is due to the action of certain enzymes which resemble carboxypeptidase or endopeptidase (catalepsin), respectively. These and other enzymes which inactivate enkephalins and endorphins are known collectively as enkephalinases and endorphinases. An enkephalinase inhibitor is a substance which inhibits a class of enzymes known as enkephalinases, an endorphinase inhibitor is a substance which inhibits a class of enzymes known as endorphinase, said enzymes destroy the neuropeptides, enkephalin and endorphin in the animal body, Blum, K., *Handbook of Abusable Drugs*, Gardner Press, New York, 1984.

Substances known to alter or decrease alcohol preference in rodents include but are not limited to alanine, fructose, amphetamine, alloxan, endorphin, methionine enkephaline, opiates, narcotic antagonists, and estrogens.

The age old question of whether alcoholism is a psychiatric illness or a biological disease with a specific cause and thus a probable "cure" is still being asked by professionals in the field and is quite controversial.

Scrutiny of the literature reveals that during the past decade certain theories on the etiology of alcoholism includes the interaction of alcohol and opiates in terms of their behavioral and pharmacological actions and resultant addiction to these psychoactive substances may be due to similar biochemical mechanisms.

Following the first suggestion of dual addiction, research in mice refuted this possibility on the basis that dependence to ethanol in mice was not altered by the narcotic antagonist, Naloxone, and according to some workers there is a lack of evidence for the relationship between ethanol and opiates. In this regard, it was stated that since the personality as well as medical symptoms of opiate addicts compared to alcoholics is so distinctly different that to consider commonality is not only improbable, it is unreasonable.

Reports from a few investigators indicated that alcohol ingestion leads to the formation of by-products termed tetrahydroisoquinolines (TIQ's) which are alkaloid condensation products of ethanol metabolism and can be found in the poppy plant where opium is extracted. In simpler terms, it was proposed that when one consumes ethanol in essence that person is ingesting an opiate. In this regard the inventors propose the "link" hypothesis whereby TIQ's can act as an opiate and thus bridge the gap between these two distinct addictive agents. This met with a series of reports which was based on empirical data refuting the "link" hypothesis. The prime controversy was that it was difficult to detect significant amounts of the TIQ's in the brains of animals exposed to ethanol.

Additional work suggests that the TIQ's directly interacts at opiate receptor sites in the brain of rodents. However it was pointed out that this interaction was at a 10-4 molar concentration in vitro assays and thus was much too weak and therefore was not considered as a strong alcohol-opiate link. Furthermore, the brain amounts of the TIQ's and metabolites in mice consuming alcohol was not considered physiologically significant. While some studies show that both the actions of ethanol and TIQ's are blocked by the narcotic antagonist, Naloxone, other research did not support these findings in both animals and humans. A most controversial finding involved the abnormal induction of alcohol drinking by infusions of a variety of TIQ's. This finding is still controversial and remains a question for study. The conclusion reached from publications which support but in no way prove the correlation between TIQ's and ethanol and opiates are: opiates and ethanol act through the opiate receptors; and TIQ's directly or indirectly interact at induced abnormal ethanol drinking in rodents.

An observation which raises an important question with regard to common receptor interaction of opiates and ethanol is that opiate addicts using methadone replacement therapy continue to have euphoriant effects from the ingestion of alcohol. In this regard there are reports showing enhanced alcohol drinking in patients receiving methadone. Without definitive experiments it is conjectured that ethanol through TIQ's act on the endogenous delta receptor site rather than the mu site and thus during mu receptor blockade with narcotics like methadone, which does not bind well to the delta site, alcohol-induced euphoria is obtained. We are further taught that pain killers like morphine do not decrease alcohol consumption and this distinguishes simple analgesia from alcohol abuse and alcoholism.

This then further raises the questions that although endorphins or enkephalins possess analgesic qualities and since ethanol is a simple two carbon molecule and not a benzyl alkaloid and is without significant analgesic properties, it is very difficult to envision a common mechanism of action of these diverse classes of drugs particularly being mediated by the endogenous endorphinergic system.

In spite of this unobvious rationale, the inventors decided to systematically determine the involvement of endorphins and enkephalins in ethanol actions. An important issue that still remains is the concept of alcoholism being genetically influenced.

Early investigations by the inventors further support the correlation between alcohol, opiates, and neuropeptidyl opiates.

In this regard the finding of alcohol preferring mice having somewhat lowered brain enkephalins compared to non-alcohol preferring mice does not answer the problem of cause and effect in terms of alcohol desire. From animal and human experiments it is not clear that brain levels of endorphins and/or enkephalins act as a determinant for craving behavior in general. In fact, there has been one study which found an environmentally-induced reduction of brain enkiphalins in rodents exposed to ethanol during gestation without having significant effects on ethanol preference of the offspring.

Neverless, the inventors describe in this application the discovery of enkephalinase and/or endorphinase inhibitors, substances which raise the levels of endogenous neuropeptidyl opiates naturally without causing addiction by themselves, as novel anti-craving agents including but not limited to alcohol abuse. It also describes the method of treatment and dosage range of certain of these enkephalinase inhibitors to interfere with the compulsive impulse to over-indulge in alcoholic beverages. It further describes the composition of a fortified combination which effects not only the endorphinergic system but also other neurotransmitter systems involved in craving behavior.

Reduced craving in human alcoholics is not achieved with typical ant-depressant medication such as tricyclic anti-depressants, or analgesic agents such as methadone wherein alcohol consumption goes up, or by disulfram therapy. Alcoholism is now classified by the National Council on Alcoholism as a biogenetic disease which is one component of a more general condition commonly known as Obsessive Compulsion Behavioral Disorder. Other types of compulsion include drug seeking, smoking, eating disorders (buleria), sexual promiscuity, and gambling. The National Council on Alcoholism recognizes alcoholism as a disease and not simply a psychosocial phenomenon and has developed definite criteria for the diagnosis and treatment of this illness.

Adult Children of Alcoholics Foundation reports twenty-eight million Americans have been recognized as potential high risk individuals. These persons have an associated syndrome which includes lowered self esteem, lack of well being, fear, anger, depression, and compulsive behavior. Alcoholism is considered to be a biogenetic disease which may be due, in part, to a brain imbalance of neuropeptidyl opiates.

SUMMARY OF THE INVENTION

The compounds described in this invention effectively prevent the destruction of endorphins; this permits the endorphins to accumulate in regions of the nervous system and exert an euphoriant action. In so doing the endorphin acts as a substitute for alcohol and stops the individual from craving alcohol.

An important feature of the subject methods and compositions is that they themselves do not produce any kind of craving, i.e., they do not cause dependence. Thus the treatment is highly effective in that it involves substituting a non-craving method and composition for one that is highly craving, namely, alcohol and opiates.

One object of this invention is to provide a safe and practical method of attaining, in mammals, reduced endogenous craving for euphoriants such as alcohol and opiates from naturally occuring enkephalins and/or endorphins.

Another object of this invention is to provide a therapeutic, anti-alcohol craving combination to assist in the eradication of the disease known as alcoholism.

DETAILED DESCRIPTION OF THE INVENTION

General Description of Tests of Individual Substances and Effect of the Substances Tested In terms of ethanol and opiate seeking behavior, the genotype theory proposes that individuals prone to such behavior possess a genetic deficiency of the endorphinergic system and both environmental conditions and long-term exposure to these drugs results in marked reduction of endogenous peptidyl opiates. Animal and human evidence which support a gene defect in the synthesis of endorphins show:

a. ethanol preferring C57BL/6J mice exhibit less brain enkephalin than non-ethanol preferring DBA2/J mice, suggestive of an inverse relationship whereby lowered endorphins equates to higher ethanol desire;

b. stress reduces brain endorphins and enhances ethanol consumption in rodents; and c. long-term of hamsters consuming ethanol resulted in marked reduction of basal ganglia leucine-enkephalin, and human alcohol and opiate addicts show a central deficiency of beta-endorphin. Since the endogenous opiates are destroyed by neuropeptidases (enkephalinase and endorphinase), enkephalinase and endorphinase inhibitors by elevating enkephalin and endorphin levels reduce ethanol consumption in inbred mice.

Experimental support for the genotype theory include:

1. Correlation between enkephalin levels and alcohol preference in a number of strains of mice.

Evidence indicates that there is a negative correlation between enkephalin levels and alcohol intake, i.e., the higher the level of brain enkephalin the lower the intake of alcohol by these mice. The correlation coefficient for experiments using several strains of mice is highly significant ($R=0.9$). Such results suggest that the driving force in humans for alcohol consumption is low enkephalin levels in the brain. Accordingly, increasing enkephalin levels in drinkers results in avoidance of alcohol intake.

These results are strengthened by additional data on two subline strains of mice with significantly different brain enkephalin levels, as shown in Table I.

TABLE I

| Subject | Methionine-Enkephalin pm/g brain | Number | Significance |
|---|---|---|---|
| C57BL/6N (Simonson) | 323.84 ± 13.58 | 10 | $p < .05$ |
| C57BL/6J (Jackson) | 289.36 ± 14.27 | 10 | |

The mice with higher methionine-enkephalin levels (C57BL/6N) drank significantly less alcohol than those of the other group (C57BL/6J) when tested over a fourteen day period.

2. Effect of chronic alcohol intake on methionine-enkephalin levels in brains of animals and humans.

Long term ethanol consumption in hamsters significantly reduces the concentration of an enkephalin-like immunoreactive substance in the basal ganglia. Other investigations found that there is a marked central deficiency of endorphins in alcoholics compared to non-alcoholics. Although these findings further support the involvement of peptidyl opiates in the action of ethanol, they are at best only suggestive that chronic alcoholism might be an endorphin deficient disease. In spite of the controversial nature of the subject, it was conjectural that giving a drug which raises the levels of endorphins reverses the disease and diminishes the need for alcohol intake. Similar results, showing marked decrease in brain enkephalin levels, have been reported during the chronic intake of narcotic drugs. Thus, craving in general results from a deficiency in endorphins.

3. Evidence that D-phenylalanine (DPA) or hydrocinnamic acid, enkephalinase inhibitors, can suppress intake of alcohol in laboratory animals.

In an ethanol acceptance experiment, chronic treatment with DPA (500 mg., two times daily, for eighteen days) compared to saline controls significantly ($p < 0.01$) reduced ethanol consumption in C57 BL/6J mice. Specifically, these alcohol preferring mice exhibited a 21% decline in alcohol consumption subsequent to DPA administration. When the DPA treated craving mice were provided a ten percent ethanol solution consumption was 2.87±0.14 ml. whereas the saline treated group was 3.72±0.14 ml. Additionally, the alcohol consumption of the DPA treated alcohol craving mice was comparable (2.87±0.14 ml.) to and not statistically different than that of the alcohol-averse DBA2/J mouse strain (3.0±0.21 ml.).

Groups of C57BL/6J mice were adminstered either cerebrospinal fluid or hydrocinnamic acid, a metabolite of DPA. The amount of alcohol consumption was measured daily over a twenty-eight day period. Results indicate that one day following administration of hydrocinnamic acid the ethanol preference ratio was 0.46±0.087 which was significantly ($p < 0.05$) lower than the control C57BL/6J mice which was 0.60±0.087. The data reveal that the second day following administration of hydrocinnamic acid, ethanol preference returned to pre-injection levels (0.70±0.087) followed by a continuous reduced intake of ethanol over a seven day period of 0.49±0.068 at the twenty-second day. Pre-injection levels of ethanol preference were observed on the twenty-second day following drug administration (0.69±0.087).

Furthermore, a significant enhancement ($p < 0.2$) of whole methionine-enkephalin levels in C57BL/6J mice treated with hydrocinnamic acid relative to controls was observed at dose levels ranging between 100, 150 and 250 mg./kg. All doses resulted in a significant increase of methionine-enkephalin over controls and were 178±8.0 (n=7), 180±8.0 (n=5), 188±20.0 (n=6) pecomoles per gram, respectively, compared to controls at 140±12.0 (n=7).

4. Effect of DL-phenylalanine on alcohol consumption and well being in humans.

In a number of case reports several comments included: no impulse to drink alcohol; a feeling of well being; and reduced anger. Other results show 66% total sobriety from 4 to 35 weeks; 33% conversion of alcoholic to social drinking (only one or two alcoholic beverages with dinner); and 100% indicate no impulse to drink alcohol. In the eleven adult children of alcoholics (ACOA), the entire group (100%) reported intense feelings of well being, relief of depression, feeling good about themselves, as well as more self control and being more calm.

PREFERRED EMBODIMENTS OF THE INVENTION

Each of the several embodiments of the invention hereinafter to be described not only reduces the intake of alcohol but also significantly alters the drug hunger associated with compulsive disorders including alcoholism. Furthermore, the sequelae associated with chronic alcohol intake including but not limited to memory deficit, trace metal deficiency, depression, anxiety, nutritional imbalance, and insomnia, are reduced.

EXAMPLE I

In this invention only and not in limitation, the term enkephalin inhibitors includes D-phenylalanine (DPA), DL-phenylalanine (DLPA), hydrocinnamic acid, and D-amino acids such as D-leucine. It is anticipated that other enkephalinase inhibitors selected from a group consisting of certain protein synthesis inhibitors (bacitracin, bestatin, and puromycin); and peptide amino acids (mono free form amino acids of the D-form, di- and tripeptides of the essential amino acids in the D-form; thiol benzyl amino acids, (2-[mercapto-3-phenyl-propanoyl]-L-leucine; carboxyalkyl methyl esters, N-[(R,S)-2-carbethoxy-3-phenyl propanol]-L-leucine; as well as a number of other structurally unrelated compounds such as secobarbital, pyrophosphate, O-phenanthroline, phosphamidon, Z-leucine-NHOH, and Z-glycine-NHOH.

In each of the formulations hereinafter given, DPA ranges from 16 to 500 mg. with a daily dosage in the range of 16 to 5000 mg.; when DPA is substituted in Examples I–XII each dose ranges from 32–1000 mg. with a daily dosage in the range of 32 to 10000 mg.; when hydrocinnamic acid is substituted in Examples I–XII each dose ranges from 1–100 mg. with a daily dosage in the range of 1 to 100 mg. Each of the enkephalinase inhibitors can be administered in liquid formulation, in powder form, and in solid dosage form, either capsules or tablets.

The potencies of the various listed enkephalinase inhibitors in vitro range from 10 nM to 1 nM amounts and, therefore, the anticipated human dosage range is from milligrams to micrograms per kilograms based on a 80 kilogram man. It is understood that the daily, recommended dosage is to be sufficient to alter the activity of enkephalinase and/or opioid receptor function so as to reduce the craving for euphoriants, such as alcohol and opiates. The broad range of dosage is provided to compensate for genetic variability and human specific pharmogenetic response. For example, N-(carbethoxymethyl)-D-phenylalanyl-D-leucine, selected from the carboxy-methylester group, the daily dosage range is between 500 and 5000 micrograms whereas the dosage range of D-leucine is between 15 and 5000 milligrams.

During the first ten weeks of therapy, the total daily dosage of each of the several components in a specific formulation preferably should not exceed the maximum given for each such component. Thereafter, the total daily intake can be reduced to one-half the respective maximum, but in no case less than the minimum specified for each such component, considered a maintenance level.

The following examples include combinations of substances which will provide enhanced anti-craving for alcohol via direct or indirect interaction with the endorphinergic system and/or opioid receptor functions.

These substances alone, in equal dosages, are less efficatious enkephalinase or endorphinase inhibitors in reducing craving but are synergistic when used in combination with said inhibitors.

EXAMPLE II

Another formulation of the subject invention is as follows:

| D-phenylalanine | 16–500 mg. |
| --- | --- |
| Lithium carbonate | 25–500 mg. |

As heretofore mentioned, the daily dosage of D-phenylalanine ranges from 16 to 5000 mg.; the daily dosage of lithium carbonate ranges from 25 to 3000 mg.

Lithium carbonate in the specified range in a selected composition is involved in altering the function of the neurotransmitters, norepinephrine and dopamine. Since there are distinct interactions between the endorphinergic system and the catecholaminergic system, lithium inhibits alcohol craving in humans. Toxic effects of lithium are, in general, dose dependent and severe reactions result when the serum level of lithium reach 2.5 mEq./liter.

Other lithium salts, including lithium citrate, may also be substituted.

EXAMPLE III

| D-phenylalanine | 16–500 mg. |
| --- | --- |
| L-glutamine | 25–500 mg. |

L-glutamine is an amino acid which is involved in the synthesis of GABA, a known inhibitory brain neurotransmitter. Increases in GABA result in reduced anxiety and alcohol consumption. The rationale for GABA as an antianxiety substance involves the characterization and identification of the benzodiazepine receptors (librium, valium to these receptors and reduce anxiety) and the intimate relationship of GABA and the benzodiazepine receptor sites.

In the formulations of Example III, L-glutamine ranges from 25 to 5000 mg. daily; THIP (4,5,6,7-tetrahydroisoyazolo-[4,5-C]-pyridin-3-OL, obtained from Lundback, Ltd. of Copenhagen, Denmark, in the daily range of 15 to 120 mg. and glycine, in the daily range of 25–3000 mg., may be substituted for the L-glutamine.

EXAMPLE IV

| D-phenylalanine | 16–500 mg. |
| --- | --- |
| L-glutamine | 25–250 mg. |
| Lithium carbonate | 25–250 mg. |

As heretofore mentioned, in said formulation, L-glutamine ranges from 25–5000 mg. daily while the said lithium salt ranges from 25–3000 mg. daily, depending on resultant individual toxic effects.

EXAMPLE V

| D-phenylalanine | 16–500 mg. |
| --- | --- |
| L-tryptophan | 25–500 mg. |

L-tryptophan is a precursor amino acid which increases levels of the sleep substance neurotransmitter, serotonin (5-hydroxytryptamine), found in high concentrations in the raphe nucleus of the brain. Serotonergic system manipulation results in alteration of alcohol consumption in rodents. Since it takes hours for the L-tryptophan to be converted to brain serotonin it is advisable to include L-tryptophan in the combination product so that if taken during the waking periods of the day, the individual will benefit in the evening. Since serotonin is rapidly metabolized under normal conditions, no accumulation effect will result in the individual and thus no adverse drowsiness will occur during the waking hours. Other serotonin receptor stimulators include mthyltryptamine and fluvoxamine. Stimulation of brain serotonin results in reduced alcohol craving in animals. In a formulation wherein DLPA is substituted for DPA, brain serotonin is usually lowered and L-tryptophan increases the same. Fluvoxamine, manufactured by Merck, Sharpe and Dohme, in the range of 25–100 mg. per dose and a daily dosage of 25–300 mg. also boosts serotonin levels.

As heretofore mentioned, in said formulation L-tryptophan ranges from 25 to 5000 mg. daily. It is anticipated that this formulation is fortified by the addition of Vitamin B6, pyridoxine hydroxide, at a dosage range of 10–600 mg. per day, to assist in the conversion of L-tryptophan in the brain to serotonin. When taken over extended periods of time, the daily dosage of Vitamin B6 should be in the range of 10–50 mg. per day.

EXAMPLE VI

| D-phenylalanine | 16–500 mg. |
| --- | --- |
| L-tryptophan | 25–250 mg. |
| Lithium carbonate | 25–250 mg. |

The daily dosages of the several constituents are specified in Examples II and V; the other specified enkephalinase inhibitors and the ranges therefor are given in Example I. As heretofore mentioned, methyltryptamine may be substituted for L-tryptophan.

EXAMPLE VII

| D-phenylalanine | 16-500 mg. |
|---|---|
| L-glutamine | 25-250 mg. |
| L-tryptophan | 25-250 mg. |

Examples III and V provide the daily dosages of the specified constituents, while Examples I and VI provide the ranges of the substitute constituents.

EXAMPLE VIII

| D-phenylalanine | 16-250 mg. |
|---|---|
| L-glutamine | 25-250 mg. |
| L-tryptophan | 25-250 mg. |
| Lithium carbonate | 25-250 mg. |

The daily dosages of the several constituents and substitutes therefor have heretofore been provided in Examples I, II, III and VI.

EXAMPLE IX

| D-phenylalanine | 16-500 mg. |
|---|---|
| L-glutamine | 25-200 mg. |
| L-tryptophan | 25-100 mg. |
| Ascorbic acid | 25-100 mg. |
| Niacinamide | 25-100 mg. |

Ascorbic acid (Vitamin C) affects the opioid receptor system and reduces opiate and alcohol withdrawal reactions; its combination with DL-phenylalanine in a number of patients has resulted in reduced alcohol impulse.

Niacinamide, 3-pyridinecarboxamide, affects the anxious state of the individual and has a positive effect during alcohol withdrawal. It is believed to affect the opioid receptor system.

EXAMPLE X

| D-phenylalanine | 16-1000 mg. |
|---|---|
| ICI 154.129 | 0.25-100 mg. |

A delta opioid receptor blocker may be defined as a substance which binds to the endogenous delta endorphinergic receptor and prevents the pharmacologic response of endorphins or other opioids. Alcohol and/or its metabolites bind to the delta receptor and produces certain pharmacologic effects including euphoria. It is understood that the utilization of such a delta opioid receptor blocker will benefit a patient undergoing detoxification and rehabilitation by virtue of blocking the euphoric effects of subsequent alcohol consumption by the patient. Aan example of a delta receptor blocker is ICI 154.129 manufactured by Imperial Chemical Industries of England.

The daily dosage range of D-phenylalanine is 16 to 5000 mg. and the daily dosage of ICI 154.129 is 1-200 mg.

EXAMPLE XI

| D-phenylalanine | 16-1000 mg. |
|---|---|
| Naltrexone | 0.25-100 mg. |

A mu opioid receptor blocker may be defined as a substance which binds to the endogenous mu or morphine-type receptor and prevents the pharmacologic response of narcotics (opioid substances). Opioid or morphine-like substances bind to the mu receptor and produce certain pharmacologic effects including euphoria. It is understood that the utilization of such a mu opioid receptor blocker benefits a patient undergoing detoxification and rehabilitation by virtue of blocking the euphoric effects of subsequent imbibing of opiates or narcotics by the patient. Examples of mu receptor blockers are Naltrexone and Naloxone, both manufactured by DuPont of Wilmington, Del.

The daily dosage range of D-phenylalanine is 16-5000 mg. and the daily dosage of Naltrexone is 1 to 200 mg.

EXAMPLE XII

| D-phenylalanine | 16-500 mg. |
|---|---|
| D-leucine | 16-500 mg. |

The daily dosage range of D-phenylalanine is 16-5000 mg. and the daily dosage range for D-leucine or any other D-amino acid is 16-5000 mg. The daily dosage of DL-leucine is 32 to 10000 mg.

In this example it is anticipated that any other enkephalinase or endorphinase inhibitor may be combined in like manner.

EXAMPLE XIII

Generally beta-endorphin as well as other endorphins of the large polypeptide character is destroyed in the body by endorphinases. Phenyl-methyl-sulfonyl-fluoride (PMSM) by Sigma Laboratories is an endopeptidase inhibitor which in vivo raises brain beta-endorphin levels at a dose range in rodents of 5-500 mg. per kilogram.

An example of an endorphinase inhibitor as an anticraving agent is as follows:

Phenyl-methyl-sulfonyl-fluoride 5-400 mg.

The daily dosage is 5 to 400 mg., as limited by resultant toxicity observed in each individual patient.

A method for calculating the anticipated human dose includes the steps of:

1. determining the in vitro molarity (molecular weight of a selected substance dissolved in a liter of solution) required to inhibit either enkephalinase or endorphinase by 100%;

2. determining the aqueous distribution fraction, that is, the amount of water within the body that the substance dissolves into;

3. multiplying the aqueous distribution fraction by the dose in molarity which is effective to reduce enzyme activity 100% by the molecular weight of the substance; and 4. multiplying the obtained number in step 3. by the weight of the subject in kilograms. This method provides a dose which is effective as an Generally, dose ranges may be extrapolated from in vitro inhibition data allowing a range factor of 10000 to compensate for factors affecting absorption, blood brain barrier transport, degradation, inactivation, body weight and in vivo compartmentilization, provided that the largest dose is non-toxic.

It should be understood, of course, that the foregoing disclosure relates to only preferred embodiments of the invention and that it is intended to cover all changes and modifications of the process and product herein chosen for the purposes of the disclosure which do not constitute departures from the spirit and scope of the invention.

What is claimed is:

1. A method for reducing the craving of a human or animal for alcohol by administering to said subject, at least one substance which inhibits the destruction of neuropeptidyl opiates in an amount sufficient to reduce the craving for alcohol.

2. A method as in claim 1 wherein the substance is D-phenylalanine.

3. The method of claim 2 wherein the daily dosage range of D-phenylalanine is 16–5000 mg.

4. A method as in claim 1 wherein the substance is DL-plenylalanine.

5. The method of claim 4 wherein the daily dosage range of DL-phenylalanine is 32–10000 mg.

6. A method as in claim 1 wherein the substance is hydrocinnamic acid.

7. The method of claim 6 wherein the daily dosage range of hydrocinnamic acid is 1–100 mg.

8. A method as in claim 1 wherein the substance administered is an effective amount of a combination of amino acids selected from the group that consists of D-phenylalanine, DL-phenylalanine, D-leucine, DL-leucine, and hydrocinnamic acid.

* * * * *